(12) United States Patent
Shesol

(10) Patent No.: US 7,780,615 B1
(45) Date of Patent: Aug. 24, 2010

(54) ANATOMICALLY DESIGNED, REUSABLE SECONDARY WOUND WRAP FOR A DIGIT

(76) Inventor: Barry F. Shesol, 18158 E. Long Ave., Aurora, CO (US) 80016

( * ) Notice: Subject to any disclaimer, the term of this patent is extended or adjusted under 35 U.S.C. 154(b) by 49 days.

(21) Appl. No.: 12/154,512

(22) Filed: May 23, 2008

(51) Int. Cl.
*A61F 5/00* (2006.01)
(52) U.S. Cl. .......................................... 602/22; 602/75
(58) Field of Classification Search ............ 602/41–42, 602/47, 59, 78–79, 20–23; 128/888, 889
See application file for complete search history.

(56) References Cited

U.S. PATENT DOCUMENTS

| | | | | |
|---|---|---|---|---|
| 2,875,758 | A | * | 3/1959 | Fuzak et al. ................... 602/58 |
| 5,456,660 | A | * | 10/1995 | Reich et al. ................... 602/79 |
| 5,843,018 | A | * | 12/1998 | Shesol et al. ................... 602/79 |
| 6,307,118 | B1 | * | 10/2001 | Reich ........................... 602/42 |

* cited by examiner

*Primary Examiner*—Michael A. Brown
(74) *Attorney, Agent, or Firm*—Edwin H. Crabtree; Ramon L. Pizarro

(57) ABSTRACT

An anatomically designed secondary wound wrap, in one embodiment, adapted for receipt around a proximal phalanx portion, distal phalanx portion, and interphalangeal joint of a digit. The wound wrap is made of a loose weave, breathable wrap material. The wound wrap includes a wrap body having a first side, a second side, a first end and a second end. The wrap body is received around the proximal phalanx portion, distal phalanx portion and interphalangeal joint. A portion of the first end extends outwardly from the wrap body for forming a first wrap holder flap, with a first hook attachment thereon. The first hook attachment is used to secure the wound wrap around the proximal phalanx portion of the digit. A portion of a second end extends outwardly from the wrap body for forming a second wrap holder flap, with a second hook attachment thereon. The second wrap holder flap extends from the wrap body in an opposite direction from the first wrap holder flap. The second hook attachment is used to secure the wound wrap around the distal phalanx portion of the digit. A primary wound dressing is received over a wound on the digit and includes a wound dressing hook attachment for attaching to an inside portion of the wrap body.

17 Claims, 3 Drawing Sheets

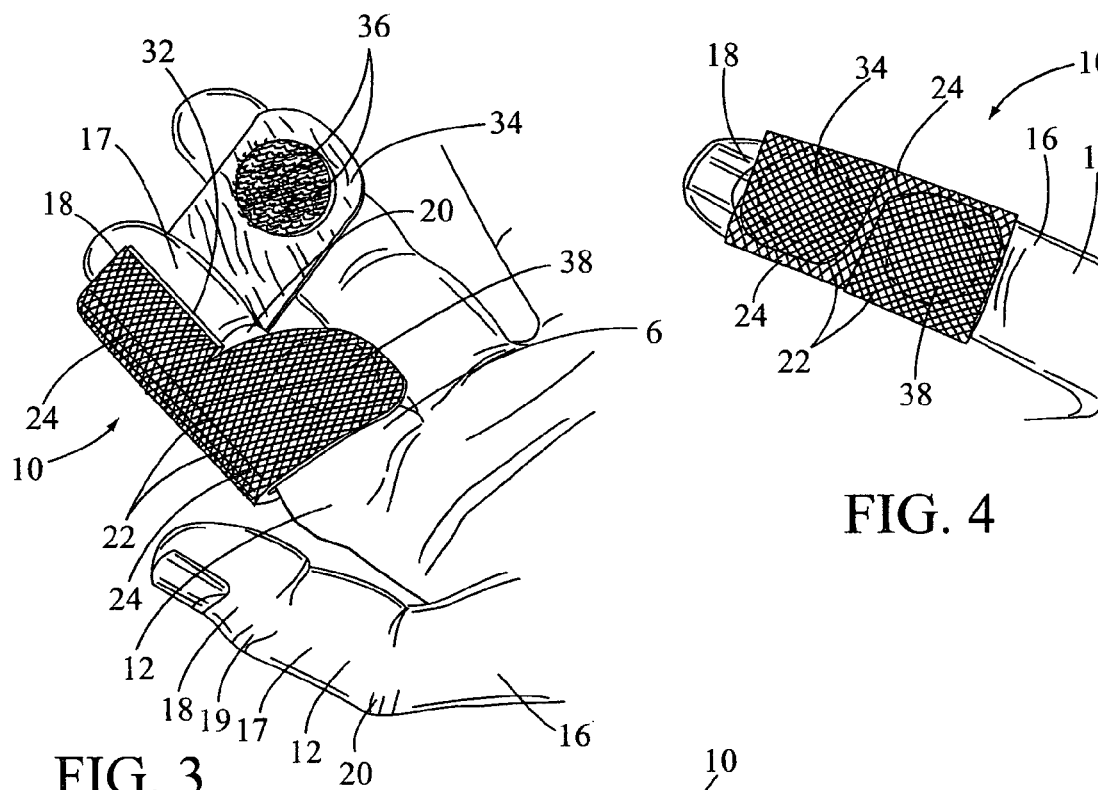
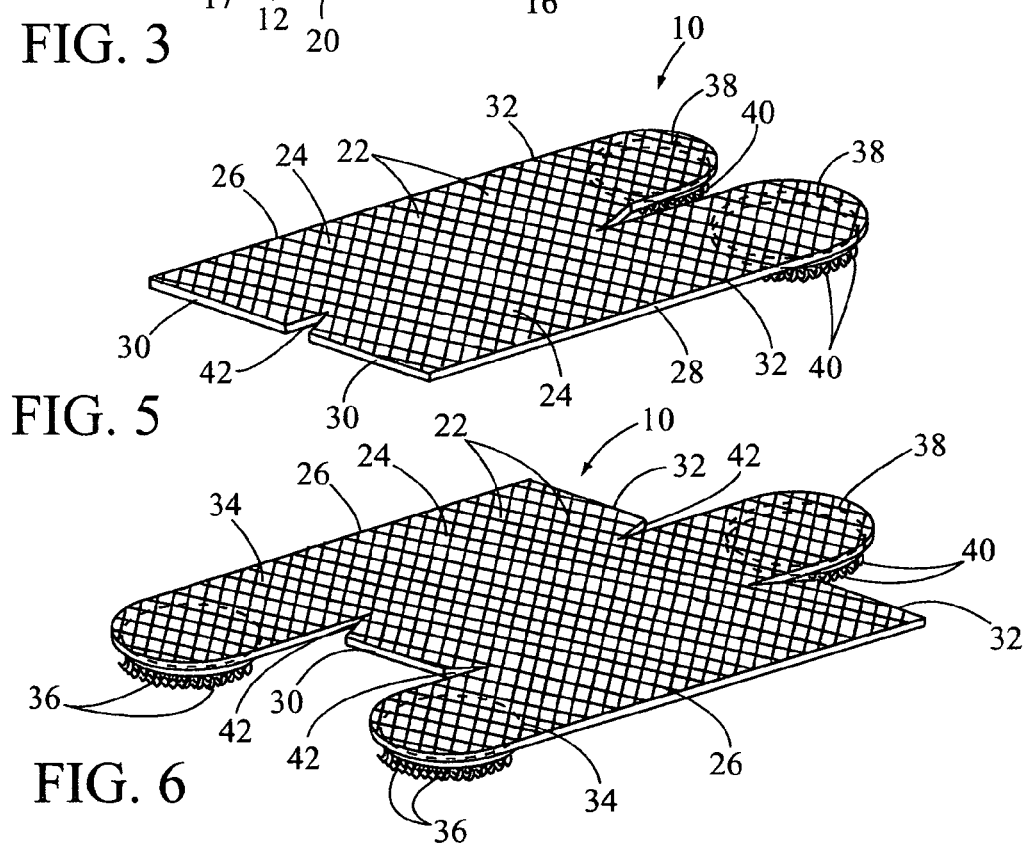

ANATOMICALLY DESIGNED, REUSABLE SECONDARY WOUND WRAP FOR A DIGIT

FIELD OF THE INVENTION

This invention relates to wound dressings and wound wraps, and particularly, but not by way of limitation, to a digit, finger or toe, secondary wound wrap. The uniqueness of this wound wrap is a function of its physical properties as well as its design so that it takes into account the anatomical features of digits and the joints of the digits, thereby providing advantages that prior art digit bandages and protective devices have failed to address.

DISCUSSION OF PRIOR ART

Heretofore, when addressing an infection or injury to a digit, the first thought as to treatment is applying a simple bandage. If indeed wound management on digits was this simple, a review of prior art would not reveal so many varied wound treatment devices. When looking further and deeper into the problems not addressed by prior art digit wound dressings and the complexities of even simple injuries or infections, it becomes clear why the subject secondary wound wrap for a digit is disclosed and claimed herein.

When treating a digit, whether a finger or a toe, there are many non-apparent factors to consider in order to achieve a successful result. For example, a simple elastic strip with a small absorbent pad fails to address the following problems and considerations, all of which either individually or in combination, can turn a minor injury into a digit loosing event:

1. Possible allergic reactions to the adhesive material used.
2. High likelihood of the surrounding tissues beneath the bandage to macerate, that is, turn the skin white and wrinkled due to high moisture contained beneath the elastic strip. The maceration destroys the skin's outer protective layer that serves to keep out bacteria and prevent further tissue loss or damage.
3. Adherence of an adhesive to the skin, producing pain on removal and stripping off of the protective layer of the skin, increasing susceptibility to bacteria. For this reason, adhesives are contraindicated for use with diabetics and individuals with vascular problems.
4. Lack of flexibility during the period of application may lead to stiffness in a joint, thus retarding the recovery, especially in elderly individuals.
5. Lacks reusability.
6. Disregard for normal anatomic functions, like joints, that affect digit mobility and effectiveness of the wound dressing.
7. Possible deleterious effects of an application that is too tight, thus limiting blood flow and fluid drainage.
8. Only provides for one type of primary wound dressing and a one time use of the device.

The following prior art patents help demonstrate the incidence and prevalence of the above problems relating to medical care of digits and why the subject invention avoids these concerns and is not only novel, but a significant, clinical improvement.

In U.S. Pat. No. 6,307,118 to Reich, a digit wrap having an ear is folded over the tip of a digit. This feature actually minimizes the individual's ability to assess the status of blood flow and the degree of tightness of the digit. Injured digits often have diminished or absent sensation. In addition, this type of digit wrap is wound circumferentially around the digit as a single piece, thereby limiting effective mobility and flexion.

In U.S. Pat. No. 7,249,385 B2 to Schukraft, a device for the digit is disclosed which serves only to protect the tip of a finger or toe. This type of protective digit device does not effectively act as a wound dressing or wound wrap.

In U.S. Pat. No. 5,333,753 to Etheridge, a finger bandage is described having an adhesive layer and an absorbent pad. The finger bandage doesn't eliminate the use of an adhesive on the bandage nor does it factor in the need to regard the interphalangeal joint, responsible for the mobility and flexion of the finger. This wound dressing only addresses the most basic type of wound dressing, which is an absorbent pad. There is no mechanism for the use of a more sophisticated type of wound dressing or for multiple use of the digit bandage.

In U.S. Pat. No. 4,615,046 to Morton, a shock absorber device is disclosed, which is not a wound healing device but a digit protective device. Additionally, this device attaches to adjoining digits and inhibits free and independent motion of the digits.

In U.S. Pat. No. 5,939,339 to Delmore et al., a self-adhering elastic bandage is described, which may be compressively wrapped around a wound. This type of compressive band is undesirable for wound healing. Furthermore, the bandage is a single piece and is not reusable once it absorbs fluids or exudate from the wound.

None of the above mentioned prior art patents provide the unique features, structure, function and advantages of the subject invention for use on wounds on digits such as fingers and toes.

SUMMARY OF THE INVENTION

In view of the foregoing, it is a primary objective of the subject invention to provide a secondary wound wrap for holding a primary wound dressing on a wound on a finger or a toe. The secondary wound wrap is used primarily for humans, but can also be used for animals under veterinarian care.

Another object and advantage of the wound wrap is it's reusable, stretchable, washable, non-constrictive, non-allergenic, non-adhesive and usable with any type of primary wound dressing used on a digit. The wound wrap material is not compressive and with normal use has 100% memory.

Yet another object and advantage of the wound wrap is that the wrap's material breathes and is permeable to air and moisture, thereby allowing air and wound drainage to pass through the wrap material and wick moisture from beneath the wrap to the outside of the wrap. This key feature allows the underlying tissues to avoid maceration and its secondary complications.

Still another object and advantage of the wound wrap is the wrap material has a loose weave texture that provides necessary loops for infinite adjustment using hook fasteners for securing the wrap around the proximal phalanx portion and the distal phalanx portion of the toe or the finger, or around the proximal phalanx portion, the middle phalanx portion and the distal phalanx portion of the finger. The wound wrap spans the proximal interphalangeal joint of the toe or finger and by attaching to the proximal phalanx portion and distal phalanx portion of the toe or finger. Also, the wound wrap can be enlarged to span both the proximal interphalangeal joint and distal interphalangeal joint of the finger. The wrap allows both the proximal interphalangeal joint and the distal interphalangeal joint to flex freely and maintain a normal range of motion.

A further object and advantage of the invention is the wound wrap is designed specifically to wrap around the digit without compromising blood flow or fluid drainage, thereby providing enhanced healing of the wound on the digit.

The subject anatomically designed secondary wound wrap for a digit, in one embodiment, is adapted for receipt around a proximal phalanx portion and distal phalanx portion of the digit and around the proximal interphalangeal joint of the digit. The wound wrap is made of a loose weave, breathable wrap material. The wound wrap includes a wrap body having a first side, a second side, a first end and a second end. The wrap body is received around the proximal phalanx portion, distal phalanx portion and interphalangeal joint. A portion of the first end extends outwardly from the wrap body for forming a first wrap holder flap, with a first hook attachment thereon. The first hook attachment is used to secure the wound wrap around the distal phalanx portion of the digit. A portion of a second end extends outwardly from the wrap body for forming a second wrap holder flap, with a second hook attachment thereon. The second wrap holder flap extends from the wrap body in an opposite direction from the first wrap holder flap. The second hook attachment is used to secure the wound wrap around the proximal phalanx portion of the digit. A primary wound dressing is received over the wound on the digit and includes a wound dressing hook attachment for attaching a portion of the wrap body.

These and other objects of the present invention will become apparent to those familiar with the use of different types of wound wraps and wound dressings when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which:

FIG. 3 is a perspective view of the wound wrap with a first wrap holder flap with first hook attachment positioned for receipt around the middle phalanx portion of the finger. A second wrap holder flap with second hook attachment is shown already secured around the proximal phalanx portion of the finger. The first and second wrap holder flaps wrapped around the finger in opposite directions.

FIG. 4 is a perspective view of the wound wrap completely secured to the finger.

FIG. 5 is another embodiment of the wound wrap having a pair of wrap holder flaps on one end of a wrap body and where the two wrap holder flaps are wrapped around the finger in one direction.

FIG. 6 is still another embodiment of the wound wrap having three wrap holder flaps for receipt around the proximal, middle and distal phalanx portions of the finger and spanning both the proximal and distal interphalangeal joints of the finger for holding one or more primary wound dressing on wounds on the finger.

DETAILED DESCRIPTION OF THE PREFERRED EMBODIMENTS

Figures 1, 2:
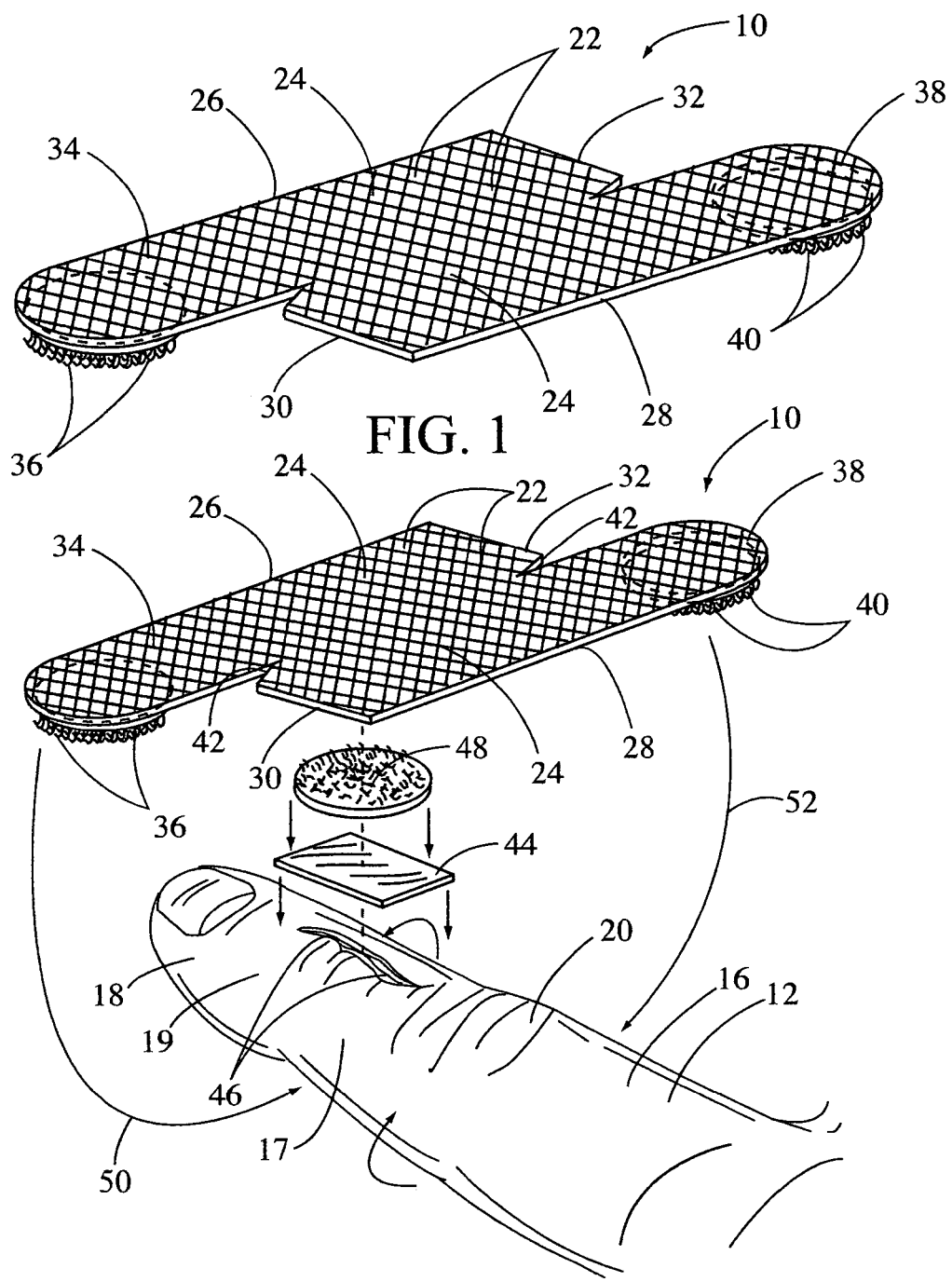
FIG. 1 is a top view of the subject secondary wound wrap and prior to receipt around a finger having a wound on the middle phalanx portion of the finger.
FIG. 2 is a perspective view of the wound wrap and positioned above a primary wound wrap disposed for receipt on the wound on the finger.

In FIG. 1, a top view of the subject secondary wound wrap is shown and having general reference numeral 10. The wound wrap 10 anatomically designed for receipt around a digit, such as a finger 12, shown in FIGS. 2-4, or a toe 14, shown in FIGS. 5 and 6. The finger 12 includes a proximal phalanx portion 16 and a middle phalanx portion 17 with a proximal interphalangeal joint 20 therebetween and a distal interphalangeal joint 19 disposed between the middle phalanx portion 17 and a distal phalanx portion 18. The toe 14 includes the proximal phalanx portion 16 and the distal phalanx portion 18 with the proximal interphalangeal joint 20 therebetween. In the anatomy of the foot, the finger 12 includes an additional joint or the distal interphalangeal joint 19 while the toe 14 does not.

The wound wrap 10 is made of a loose weave, stretchable, breathable, non-allergenic and non-adhesive material 22 and is reusable on various types and shapes of primary wound care dressings. The wrap 10 includes a wrap body 24 having a first side 26, a second side 28, a first end 30 and a second end 32. The wrap body 24, when attached to the digit, is received around the proximal phalanx portion 16, distal phalanx portion 18 and interphalangeal joint 20.

A portion of the first end 30 extends outwardly from the wrap body 24 for forming a first wrap holder flap 34, with a first hook attachment 36 thereon. The first hook attachment 36 can be a hook dot having an adhesive on its back side for securing it to the flap 34. The front side of the hook dot includes a plurality of small hooks for releasable attachment to loop material, which is part of the loose weave construction of the material 22. The first hook attachment 36 is used to engage a portion of the wrap body 24 and secure the wound wrap 10 around the middle phalanx portion 17 of the finger 12.

A portion of a second end 32 extends outwardly from the wrap body 24 for forming a second wrap holder flap 38 with a second hook attachment 40 thereon. The second wrap holder flap 38 extends outwardly from the wrap body 24 in an opposite direction from the first wrap holder flap 34. The second hook attachment 40 is used to engage a portion of the wrap body 24 and secure the wound wrap 10 around the proximal phalanx portion 16 of the finger 12. By securing the first and second wrap holder flaps 34 and 38 in opposite directions, the wound wrap 10 is held securely in place on the digit as opposed to a typical wound wrap that is wrapped around the digit in a single direction and can easily become undone.

Also, it should be mentioned that the wrap body 24 includes slits 42 therein in the first and second ends 30 and 32 and next to the first and second wrap holder flaps 34 and 38. This feature prevents the wrap 10 from gathering and bunching in this area of the wrap as it's secured to the digit.

In FIG. 2, a perspective view of the wound wrap 10 is shown positioned above a primary wound dressing 44 disposed for receipt on top of a wound 46 in the middle phalanx portion 17 of the finger 12. The top of the primary wound dressing 44 includes a wound dressing hook attachment 48, which is similar to hook attachments 36 and 40, and is used to hold the primary wound dressing 44 on a selected location on the inside of the wrap body 22. As mentioned above and through the use of the hook attachments and the loose weave material 22 used in the wrap 10, infinite adjustments can be made for loosing and tightening the wrap on the digit along with proper adjustment of the primary wound dressing on the wrap. The infinite adjustments on the wrap 10 are important, because there is swelling of the digit initially and as the wound begins to heal, the reusable wound wrap 10 can be tightened accordingly. Also it should be mentioned that the hook attachments are washable and usable on the wound wrap 10, while the primary wound dressing 44 is changed periodically.

While the hook attachments or hook dots are shown in the drawings and discussed herein as a preferred means for quick release on the wrap 10, it should be kept in mind other attachment means, such as releasable adhesives, can be used equally well, but these types of adhesives are not necessarily washable and reusable.

In this drawing, the first wrap holder flap 34 is shown ready to be wrapped around the middle phalanx portion 18 of the finger 12, as indicated by arrow 50. Likewise, the second wrap holder flap 38 is shown ready to be wrapped around the proximal phalanx portion 16 of the finger 12 in an opposite direction, as indicated by arrow 52.

In FIG. 3, a perspective view of the wound wrap 10 is shown with the first wrap holder flap 34 with first hook attachment 36 positioned for receipt around the distal phalanx portion 18 of the finger 12 and ready for attachment to the wrap body 24. The second wrap holder flap 38 with second hook attachment 40 is shown already secured around the proximal phalanx portion 16 of the finger 12. It is important to point out again that a key feature of the subject wound wrap 10 is the wrap body 24 is designed to span across the interphalangeal joint 20 of the digit. But, by attaching the wrap to the proximal phalanx portion 16 and the distal phalanx portion 18 of the digit, the interphalangeal joint 20 is free to flex and maintain a normal range of motion without the interference of the wound wrap thereon.

In FIG. 4, a perspective view of the wound wrap 10 is shown with the first and second wrap holder flaps 34 and 38 secured to the wrap body 22 completely secured around the finger 12 and holding the primary wound dressing 44 in place on the wound 46.

In FIG. 5, another embodiment of the wound wrap 10 is illustrated having a pair of second wrap holder flaps 38 with hook attachments 40 thereon and extending outwardly from the second end 32 of the wrap body 24. In this example of the wound wrap 10, the second wrap holder flaps 38 are wrapped around the finger 12 in one direction. Obviously, the wound wrap 10 can be made with a pair of first wrap holder flaps 34 rather then the second wrap holder flaps 38.

In FIG. 6, still another embodiment of the wound wrap 10 is shown having a pair of first wrap holder flaps 34 extending outwardly from the first end 30 of the wrap body 24 and a second wrap holder flap 38 extending outwardly from the second end 32 in an opposite direction to the pair of first wrap holder flaps 34. This embodiment of the wound wrap 10 is important in that it can be received around the proximal, middle and distal phalanx portions of the finger, with the finger having multiple wounds and holding a plurality of primary wound dressings 44 thereon. In this example, the wound wrap 10 spans both the distal interphalangeal joint 19 and the proximal interphalangeal joint 20 of the finger 12 and provides for freedom of movement and flexibility of the finger.

Figure 7:
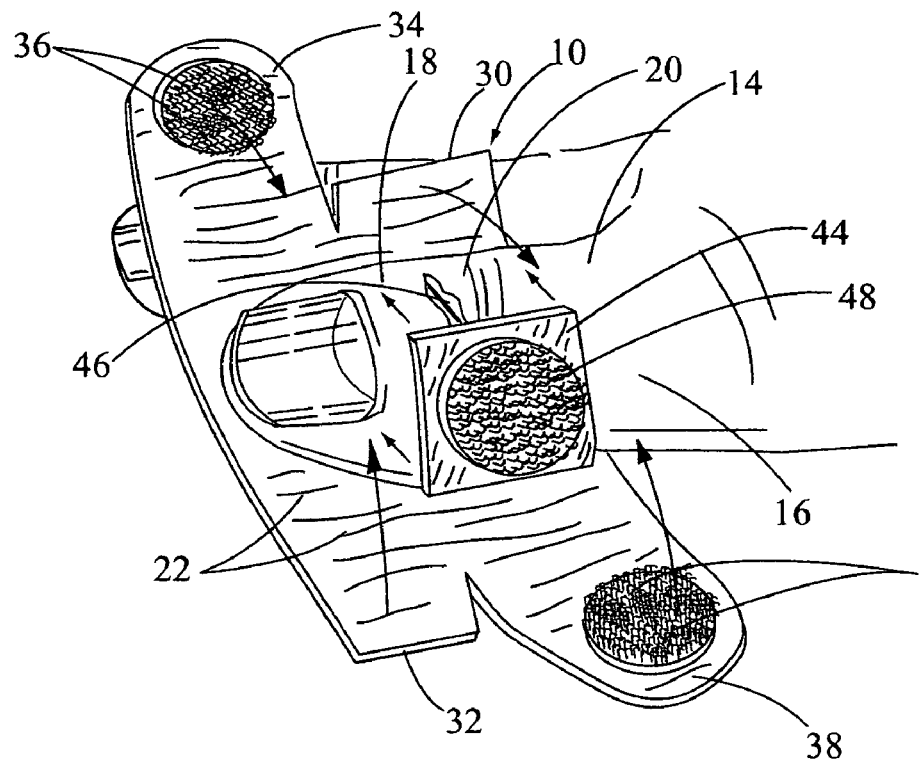
FIG. 7 is a perspective view of a toe having a primary wound dressing received on a wound on the distal phalanx portion of the toe and the secondary wound wrap positioned for be secured thereto.

In FIG. 7, a perspective view of the toe 14 is shown and having the primary wound dressing 44 ready for receipt on the wound 46 on the distal phalanx portion 18 of the toe 14. In this drawing, the secondary wound wrap 10 is positioned for the first and second wrap holder flaps 34 and 38 to be wrapped around the proximal and distal phalanx portions 16 and 18 of the toe 14 and secured to the wrap body 24.

Figure 8:
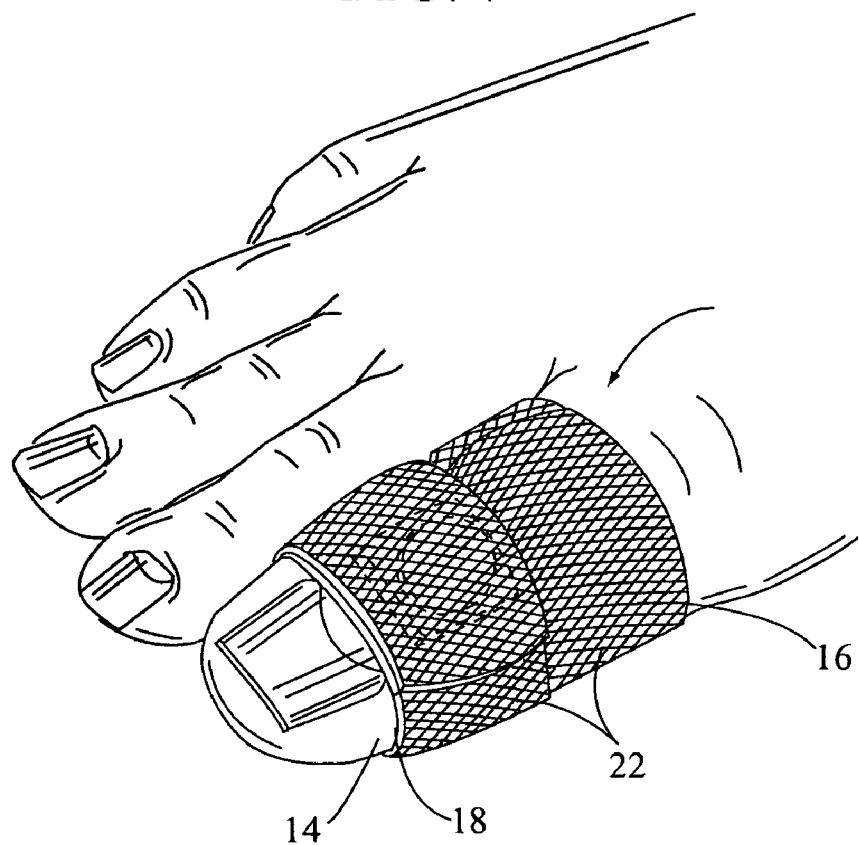
FIG. 8 is a perspective view of the wound wrap completely secured to the toe shown in FIG. 5.

In FIG. 8, a perspective view of the wound wrap 10 is illustrated completely secured around the toe 14 for holding the primary wound dressing 44 in place over the wound 46. Obviously, because the wound wrap is washable and reusable, it can be used continuously as the primary wound dressing 44 is removed and replaced during the wound healing process.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. An anatomically designed secondary wound wrap adapted for receipt around a proximal phalanx portion, a distal phalanx portion, and an interphalangeal joint of a digit, the wound wrap comprising:
   a wrap body having a first side, a second side, a first end and a second end, the wrap body adapted for receipt around the proximal phalanx portion, the distal phalanx portion and the interphalangeal joint of the digit;
   a first wrap holder flap extending outwardly from a portion of the first end of the wrap body, the first wrap holder flap having first attachment means thereon and used for releasable engagement on a portion of the wrap body for securing the wound wrap around the distal phalanx portion of the digit;
   a second wrap holder flap extending outwardly from a portion of the second end of the wrap body, the second wrap holder flap extending outwardly from the wrap body in an opposite direction to the first wrap holder flap, the second wrap holder having a second attachment means thereon and used for releasable engagement on a portion of the wrap body for securing the wound wrap around the proximal phalanx portion of the digit; and
   a joint flex line disposed along a length of the wrap body between the first end and the second end of the wrap body, the joint flex line halfway between the first side and the second side of the wrap body, the joint flex line providing freedom to flex the interphalangeal joint and maintain a normal range of motion of the digit without the interference of the wound wrap thereon when the first wrap holder flap secures a portion of the wrap body around the distal phalanx portion of the digit and the second wrap holder flap secures a portion of the wrap body around the proximal phalanx portion of the digit.

2. The wound wrap as described in claim 1 wherein the first and second attachment means are first and second hook attachments for releasable engagement of a portion of the wrap body.

3. The wound wrap as described in claim 2 wherein the wrap body and the first and second wrap holder flaps are made of a stretchable, breathable, loose weave material, the loose weave material providing loops formed therein for engaging the first and second hook attachments.

4. The wound wrap as described in claim 1 further including a primary wound dressing with wound dressing attachment means for attaching the primary wound dressing to a portion of an inside of the wrap body.

5. The wound wrap as described in claim 4 wherein the primary wound dressing attachment means is a wound dressing hook attachment for releasable engagement of a portion of the inside of the wrap body.

6. The wound wrap as described in claim 1 having slits in the first and second ends of the wrap body and next to the first and second wrap holder flaps, the slits preventing the wound wrap from gathering and bunching up when the wound wrap is secured on a digit.

7. An anatomically designed secondary wound wrap adapted for receipt around a proximal phalanx portion, a distal phalanx portion, and an interphalangeal joint of a digit, the wound wrap comprising:

a wrap body having a first side, a second side, a first end and a second end, the wrap body adapted for receipt around the proximal phalanx portion, the distal phalanx portion and the interphalangeal joint of the digit;

a first wrap holder flap extending outwardly from a portion of the first end of the wrap body, the first wrap holder flap having a first attachment means thereon and used for releasable engagement on a portion of the wrap body for securing the wound wrap around the distal phalanx portion of the digit;

a second wrap holder flap extending outwardly from a portion of the first end of the wrap body, the second wrap holder flap extending outwardly from the wrap body in the same direction as the first wrap holder flap, the second wrap holder having a second attachment means thereon and used for releasable engagement on a portion of the wrap body for securing the wound wrap around the proximal phalanx portion of the digit;

whereby the wrap body and the first and second wrap holder flaps are made of a loose weave, stretchable, breathable material, the loose weave material providing loops therein for engaging the first and second attachment means on the first and second wrap holder flaps; and a joint flex line disposed along a length of the wrap body between the first end and the second end of the wrap body, the joint flex line halfway between the first side and the second side of the wrap body, the joint flex line providing freedom to flex the interphalangeal joint and maintain a normal range of motion of the digit without the interference of the wound wrap thereon when the first wrap holder flap secures a portion of the wrap body around the distal phalanx portion of the digit and the second wrap holder flap secures a portion of the wrap body around the proximal phalanx portion of the digit.

8. The wound wrap as described in claim 7 wherein the first and second attachment means are first and second hook attachments for releasable engagement of a portion of the wrap body.

9. The wound wrap as described in claim 7 further including a primary wound dressing with wound dressing attachment means for attaching the primary wound dressing to a portion of an inside of the wrap body.

10. The wound wrap as described in claim 9 wherein the wound dressing attachment means is a wound dressing hook attachment for releasable engagement of a portion of the inside of the wrap body.

11. The wound wrap as described in claim 10 having slits in the first and second ends of the wrap body and next to the first and second wrap holder flaps, the slits preventing the wound wrap from gathering and bunching up when the wound wrap is secured on a digit.

12. An anatomically designed secondary wound wrap adapted for receipt around a proximal phalanx portion, a middle phalanx portion, a distal phalanx portion, a proximal interphalangeal joint and a distal interphalangeal joint of a finger, the wound wrap comprising:

a wrap body made of a loose weave material and having a first side, a second side, a first end and a second end, the wrap body adapted for receipt around the proximal phalanx portion, the middle phalanx portion, the distal phalanx portion, the proximal interphalangeal joint and the distal interphalangeal joint of the finger;

a pair of first wrap holder flaps made of a loose weave material and extending outwardly from a portion of the first end of the wrap body, the first wrap holder flaps having a first attachment means thereon and used for releasable engagement on a portion of the loose weave material on the wrap body for securing the wound wrap around the proximal phalanx portion and distal phalanx portion of the finger;

a second wrap holder flap made of loose weave material and extending outwardly from a portion of the second end of the wrap body, the second wrap holder flap extending outwardly from the wrap body in an opposite direction to the first wrap holder flaps, the second wrap holder having a second attachment means thereon and used for releasable engagement on a portion of the loose weave material on the wrap body for securing the wound wrap around the middle phalanx portion of the finger;

a first joint flex line disposed along a length of the wrap body between the first end and the second end of the wrap body, the first joint flex line between the first side and the second side of the wrap body, the joint flex line providing freedom to flex the distal interphalangeal joint and maintain a normal range of motion of the digit without the interference of the wound wrap thereon when one of the first wrap holder flaps secures a portion of the wrap body around the distal phalanx portion of the digit and the second wrap holder flap secures a portion of the wrap body around the middle phalanx portion of the digit; and a second joint flex line disposed along a length of the wrap body between the first end and the second end of the wrap body, the second joint flex line between the first side and the second side of the wrap body, the second joint flex line providing freedom to flex the proximal interphalangeal joint and maintain a normal range of motion of the digit without the interference of the wound wrap thereon when the other first wrap holder flap secures a portion of the wrap body around the proximal phalanx portion of the digit.

13. The wound wrap as described in claim 12 wherein the first and second attachment means are first and second hook attachments for releasable engagement on a portion of the loose weave material of the wrap body.

14. The wound wrap as described in claim 12 further including a primary wound dressing with wound dressing attachment means for attaching the primary wound dressing to a portion of the loose weave material on an inside of the wrap body.

15. The wound wrap as described in claim 14 wherein the wound dressing attachment means is a wound dressing hook attachment for releasable engagement of the portion of the inside of the wrap body.

16. The wound wrap as described in claim 12 further including a plurality of wound dressings with wound dressing attachment means for attaching the primary wound dressings on various portions of the loose weave material on the inside of the wrap body.

17. The wound wrap as described in claim 16 wherein the wound dressing attachment means on the wound dressings are wound dressing hook attachments for releasable engagement to the various portions of the loose weave material on the inside of the wrap body.

* * * * *